United States Patent [19]
Bennett

[11] Patent Number: 5,335,672
[45] Date of Patent: Aug. 9, 1994

[54] DUAL ACTION COCKING MECHANISM FOR ADJUSTABLE BIOPSY DEVICE

[76] Inventor: LaVon L. Bennett, 354 N. 424 East, Alpine, Utah 84004

[21] Appl. No.: 157,652

[22] Filed: Nov. 24, 1993

[51] Int. Cl.$^5$ .............................................. A61B 10/00
[52] U.S. Cl. .................................................. 128/754
[58] Field of Search ............... 128/749, 751, 753, 754; 606/167, 170, 171

[56] References Cited

U.S. PATENT DOCUMENTS

| | | | |
|---|---|---|---|
| 4,699,154 | 10/1987 | Lindgren | 128/754 |
| 4,776,346 | 10/1988 | Beraha et al. | 128/754 |
| 5,014,717 | 5/1991 | Lohrman | 128/754 |
| 5,156,160 | 10/1992 | Bennett | 128/754 |
| 5,188,118 | 2/1993 | Terwilliger | 128/753 |

*Primary Examiner*—Max Hindenburg
*Attorney, Agent, or Firm*—Terry M. Crellin

[57] ABSTRACT

An improvement in a tissue sampling apparatus of the type comprising (a) an elongate housing, (b) a knob at the first end of the housing, (c) first and second pistons extending from the second end of the housing, (d) connections on the extending ends of the pistons for connecting a biopsy needle, (e) first and second springs in the housing against which the first and second pistons, respectively, are cocked so that the springs apply a biasing force against the respective pistons, (f) a trigger for releasing the first and second pistons to move in successive movements wherein the first piston moves first to its fully extended position under the biasing force of the first spring while the second piston remains in its cocked position, and after the first piston has moved to its fully extended position, the second piston moves to its fully extended position under the biasing force of the second spring. The improvement involves the cocking mechanism wherein the first and second pistons are moved to their cocked positions in separate distinct operations. The improved cocking mechanism comprises an annular ring near the second end of the housing. As the annular ring is rotated, it moves the second piston into its cocked position. The knob on the first end of the housing is pulled in a direction away from the first end of the housing to move the first piston into its cocked position.

8 Claims, 5 Drawing Sheets

DUAL ACTION COCKING MECHANISM FOR ADJUSTABLE BIOPSY DEVICE

BACKGROUND OF THE INVENTION

1. Related Patent

This application is an improvement upon a biopsy device disclosed in U.S. Pat. No. 5,156,160 issued on Oct. 20, 1992 and the entire contents of that patent are incorporated herein by reference.

2. Field of the Invention

This invention relates generally to an apparatus and method for sampling tissue. More specifically, the present invention relates to a biopsy device which can be adjusted to allow precise amounts of sample tissue to be collected thereby.

3. Prior Art

The removal of minute tissue samples from humans and animals by introducing a needle into the body and catching the sample within the needle, is a frequently used medical practice today. Such samples are necessary for microscopic examination, organ cultures, etc.

The method most commonly followed for obtaining tissue samples has been to use a needle which is formed of an inner solid rod which has a sampling notch in the distal end thereof, in conjunction with a hollow outer cannula which slides thereover and cuts tissue which has been located in the sampling notch of the inner rod. The inner rod, except for its pointed distal end, is located within the cannula when the device is inserted into the tissue to be sampled. The outer cannula is then held stationary while the inner rod is inserted deeper into the tissue. While in this position, tissue moves into the sampling notch of the inner rod just adjacent the pointed distal tip thereof. The inner rod is then held stationary while the outer cannula is slid thereover. Motion of the outer cannula passing over the sampling notch causes the tissue located therein to be severed from surrounding tissue and thereafter to be trapped in the sampling notch as the cannula completely covers the inner needle distal end. Both the outer cannula and the inner rod with the tissue sample secured therein are then simultaneously removed from the patient. The outer cannula is then slid back away from the distal end of the inner rod to allow removal of the tissue sample from the sampling notch thereof. The tissue sample is then examined.

This general method of tissue sampling has been used for several decades and is exemplified in U.S. Pat. No. 3,477,423. As disclosed therein, the needle movements are made manually. This has certain disadvantages, in that movements may not be made fast enough to insure clean and complete severance of a tissue sample. Further, manual operation of the needle generally involves inaccurate movements, and slight lack of coordination between the needle and the cannula. This often causes unnecessary tissue damage and, in the case of infectious or tumorous tissue, can cause spreading of the diseased tissue throughout a larger tissue area. Also, during manual operation of a needle, the patient may move slightly during the introduction thereof into the tissue and cause the needle to its target area. Also, respiratory movements are common for some organs, for example the liver and the kidney, which further may reduce the accuracy of the sampling technique.

An improvement in the above mentioned method of biopsy sampling has been to restrict needle movements by containing the inner rod and outer cannula inside a holder. The holder restricts needle movement to specific directions and also may carry springs therein which drive the rod and cannula through their sampling motions in a rapid and predictable manner. This technique is exemplified in U.S. Pat. No. 4,699,154. Even though this is an improvement over manually actuated needles, it nevertheless carries several disadvantages. For example, the length of the needle movement cannot be adjusted according to the size of the sample desired to be taken. Therefore, unnecessary quantities of tissue may be removed from the tissue sample area causing unnecessary tissue damage and possibly unnecessary spreading of diseased tissue. Further, the forceful introduction of a needle into the tissue area generally causes a certain amount of damage to the tissue in the immediate surroundings of the target area. This is due to the high pressure released from the needle in the injection process.

Therefore, there has long existed a problem in the prior art of controlling the size of a tissue sample taken by the biopsy needle. The size of the sample should not exceed the necessary amount of tissue needed for diagnostic purposes. Since prior art devices have included no ability to adjust the size of sample taken in an accurate manner, they have failed to resolve this problem. Also, a smaller tissue target area, such as a lesion or tumor or the like should be sampled with a shorter movement of the needle and a smaller and more controlled sample size taken thereby. This is because the needle should not pass outside the target area into unaffected area of the tissue, nor should it reach outside of the organ, tumor, lesion, etc. which is being sampled to thereby cause risk of damage to other structures such as adjacent large blood vessels or the like. It is therefore needful to develop an apparatus where the needle movements can be precisely made to allow the physician to collect precisely the desired tissue sample volume predetermined with various imaging methods (e.g. radiological, ultrasound or computer tomography examination without unnecessary damage to the tissue or surrounding structures.

In my previous patent, U.S. Pat. No. 5,156,160, there is provided a tissue sampling device which is adjustable so that various tissue sample sizes may be collected by the same apparatus depending on the pre-set adjustment thereto. The device disclosed in that patent employs a sampling needle having an inner rod and outer cannula wherein the inner rod contains a sampling notch and in which the apparatus can control the depth of penetration of the inner rod into the sampling target area in order to control the volume of tissue sample collected.

OBJECTS AND SUMMARY OF THE INVENTION

It is an object of the present invention to provide several advantageous improvements to the sampling device that was disclosed in my previous U.S. Pat. No. 5,156,160.

A particular object of the present invention is to provide improved means of cocking the first and second pistons of the tissue sampling device.

Another object of the present invention is to provide a rotating ring near the distal end of the housing of the tissue sampling device for independently cocking the second piston of the device.

A further object of the present invention is to provide a pull knob at the proximal end of the housing that can be pulled away from the housing to cock the first piston of the tissue sampling device.

A still further object of the invention is to provide improved engagement means between the first piston of the tissue sampling device and the pull knob, wherein the amount of travel of the first piston, and thus the size of the sample of the tissue taken, can be adjusted by rotating the knob.

It is also an object of the present invention to provide a transparent window in the sidewall of the housing of the tissue sampling device whereby a marker on the engagement means can be viewed to allow precise setting of the amount of travel of the first piston and thus the size of the tissue sample that is taken.

An additional object of the present invention is to provide an improved plastic cover that can enclose the portions of the first and second pistons of the tissue sampling device that extend from the distal end of the housing of the device, with the cover being easily opened and closed to allow installation and removal of the sampling needle system from engagement with the first and second pistons of the device.

The basic tissue sampling device as illustrated and described in my previous U.S. Pat. No. 5,156,160, includes an elongated generally cylindrical housing having a pair of piston like moveable elements. The first piston includes an attachment means thereon for engaging the hub portion of an inner rod of a biopsy needle, and the second piston includes means for engaging the hub portion of the outer cannula portion of a biopsy needle. The pistons extend from the housing of the biopsy device in a manner which allows for the engagement of the biopsy needle to the first and second pistons of the device. The opposite ends of the pistons are located within the housing of the biopsy device and are spring loaded to a uniquely designed releasing mechanism which, when triggered activates a first stage motion that extends the first piston (and thereby the inner rod of the biopsy needle) a predetermined distance into a tissue sample target area.k A second stage motion follows the first stage and moves the second piston in the same direction of motion as the first piston previously moved, thus moving the outer cannula to severe tissue in the sample notch of the inner rod as it re-extends thereover. Improved means are provided by the present invention, as will be discussed hereinafter, for adjustment of the distance that the primary piston is allowed to travel.

The triggering mechanism of the basic tissue sampling device of my previous U.S. Pat. No. 5,156,160, included a triggering knob located externally of the housing of the biopsy device at the proximal end of the housing. Depressing the triggering knob actuates the successive motions of the first and second pistons. Motion of the first piston is arrested at its desired length of travel by an adjustable travel member, and the movement of the second piston is initiated at the completion of the its travel of the first piston. In accordance with the present invention, improved means are provided with the triggering knob whereby the triggering knob is also used in cocking the first piston of the device. This cocking of the first piston using the triggering knob is an action separate and apart from the action of cocking of the second piston. Cocking of the second piston is achieved by rotating a ring near the distal end of the housing as will be described in detail hereinafter.

Additional objects and features of the invention will become apparent from the following detailed description, taken together with the accompanying drawings.

DETAILED DESCRIPTION OF THE PREFERRED EMBODIMENT

Figures 1, 7:
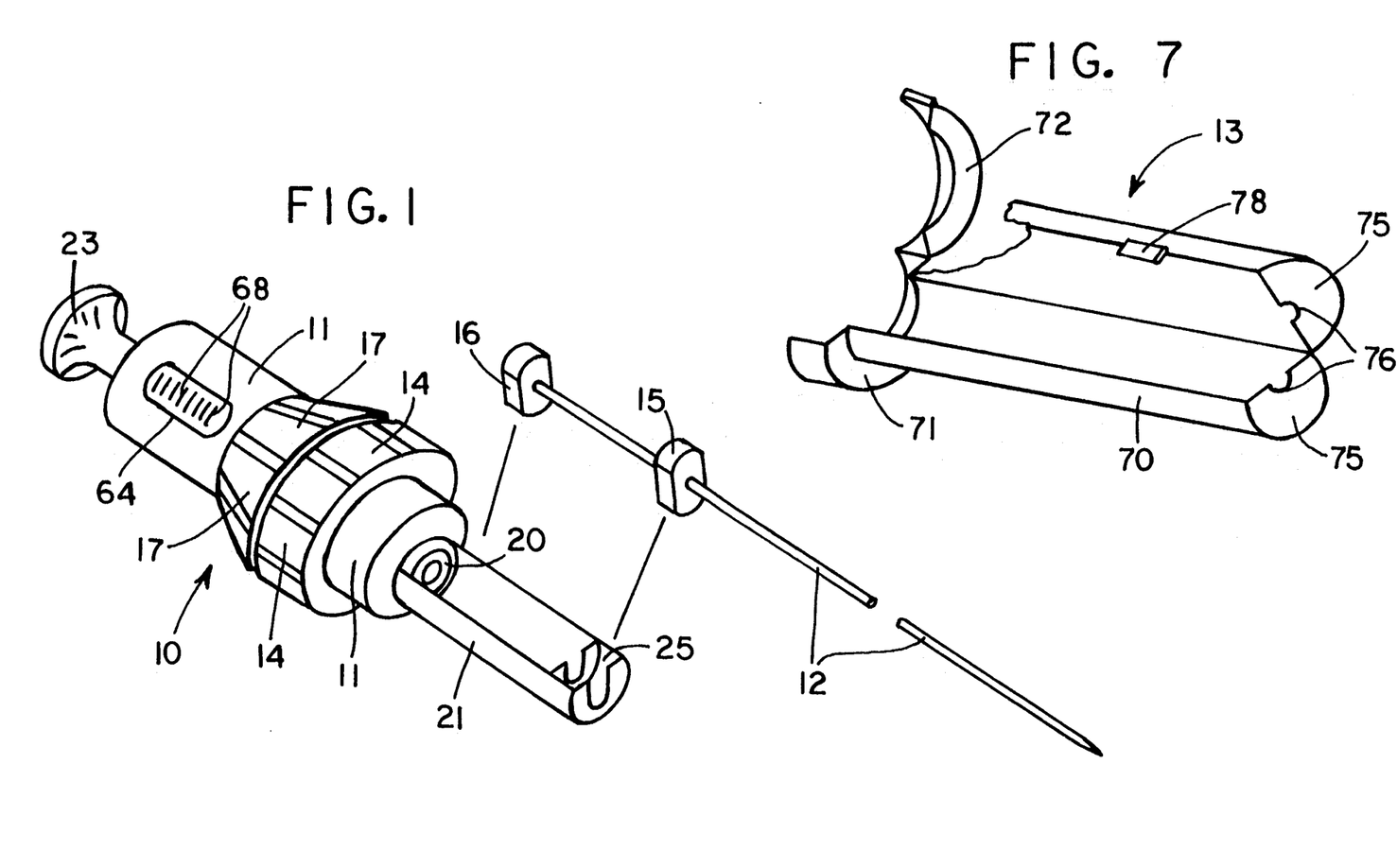
FIG. 1 is an expanded prospective view of a biopsy device made in accordance with the principles of the present invention.
FIG. 7 is a pictorial view of the removable cover that can be attached to the distal end of the housing of the biopsy device of the present invention.
Figure 2:
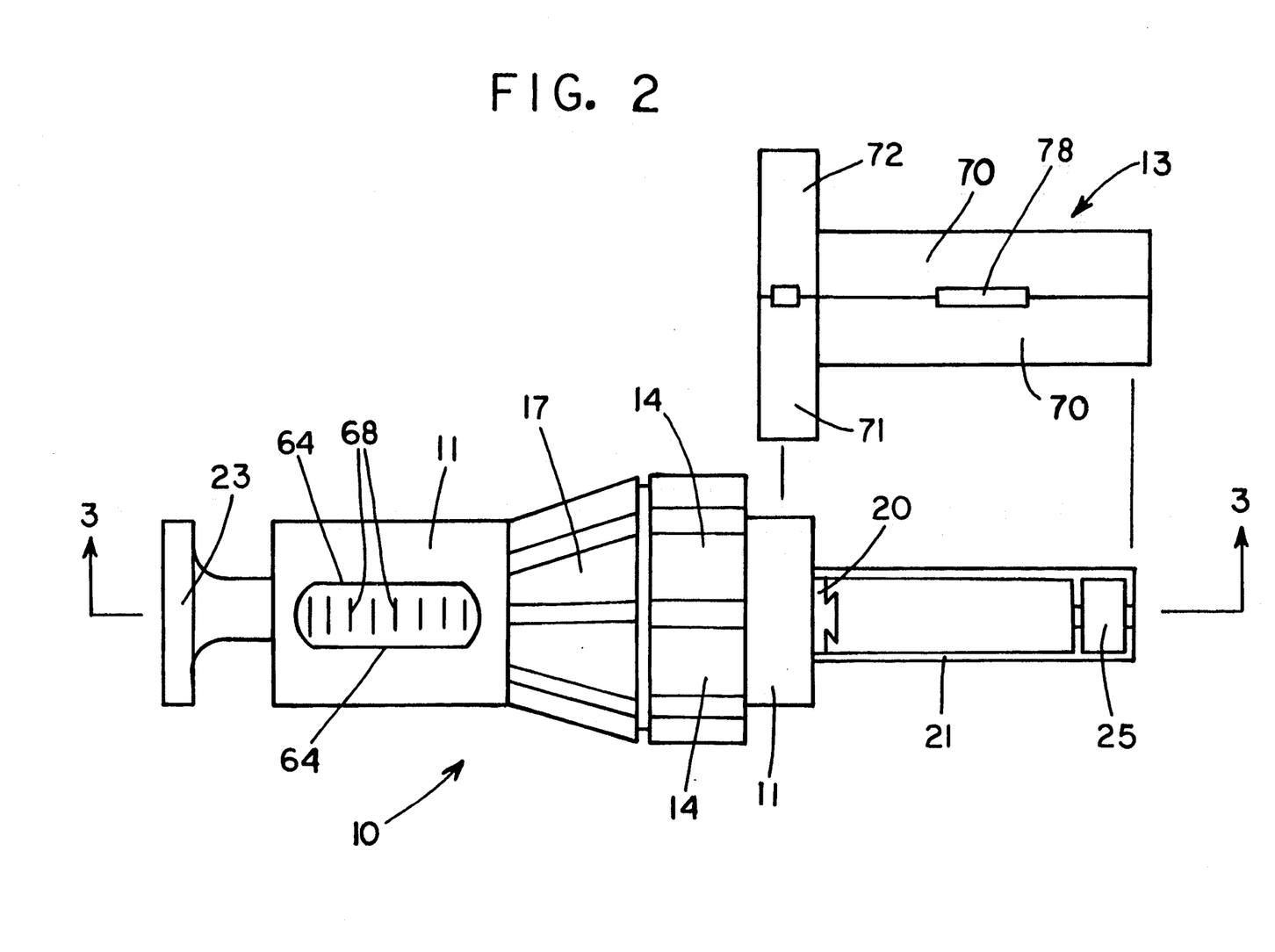
FIG. 2 is a side view of the biopsy device of the present invention showing a removable cover at the distal end of the housing of the device, with the cover being shown removed from the device.
Figures 5, 6:
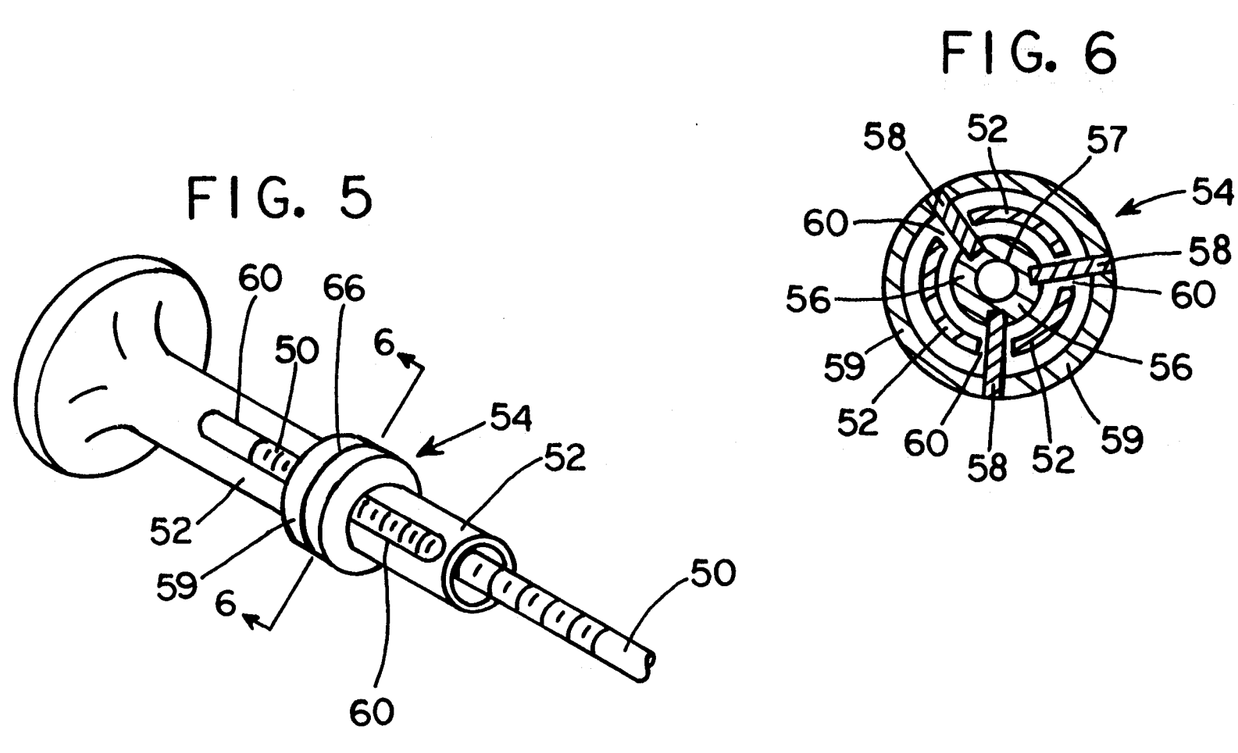
FIG. 5 is an exploded pictorial view of the distal end of the hollow shaft of the pull knob and the travel member that is threaded on the threaded end of a central shaft extending from the first piston and engages the hollow shaft of the pull knob.
FIG. 6 is a cross section taken along line 6—6 of FIG. 5.

As shown in FIGS. 1 and 2, the biopsy device 10 of the present invention comprises an elongate housing 11, a needle 12, and a removable cover 13 (the cover 13 being shown in FIGS. 2 and 6). The proximal end portion of the needle 12 is adapted to be inserted into a hollow end portion of a second piston 21 that extends from the distal end of the housing 11. The needle has two hubs 15 and 16. Hub 15 is attached to the proximal end of a cannula that forms part of the needle 12. Hub 16 is attached to the proximal end of an inner rod that passes through the cannula. The structure and operation of the needle 12 are described fully in my previous U.S. Pat. No. 1,156,160, and will not be described further herein, other than to point out that the hub 15 is received in an engagement well 25 in the distal end of the second piston 21, and the hub 16 is adapted to engage the distal end of the first piston 20 that extends from the distal end of the housing 11 into the hollow end portion of the second piston 21.

As illustrated in FIG. 2, the cover 13 fits over and around the hollow end portion of the second piston 21 that extends from the distal end of the housing 11. As will be explained hereinafter, the cover 13 can be opened so as to allow inserting and removing the needle 12 from the hollow portion of the second piston 21.

A cocking ring 14 is provided near the distal end of the housing and is used, as will be described fully hereinafter to cock the second piston 21. An annular, notched, stationary grip member 17 can be provided around the housing 11 adjacent to the cocking ring 14 to aid in manually gripping the housing 11 as the cocking ring 14 is turned to cock the second piston 21. A knob 23 is provided at the proximal end of the housing 11 which as will be described hereinafter is used to cock the first piston 20, to adjust the amount of travel of the first piston 20 and to trigger the moving motion of the first and second pistons 20 and 21.

Figure 3:
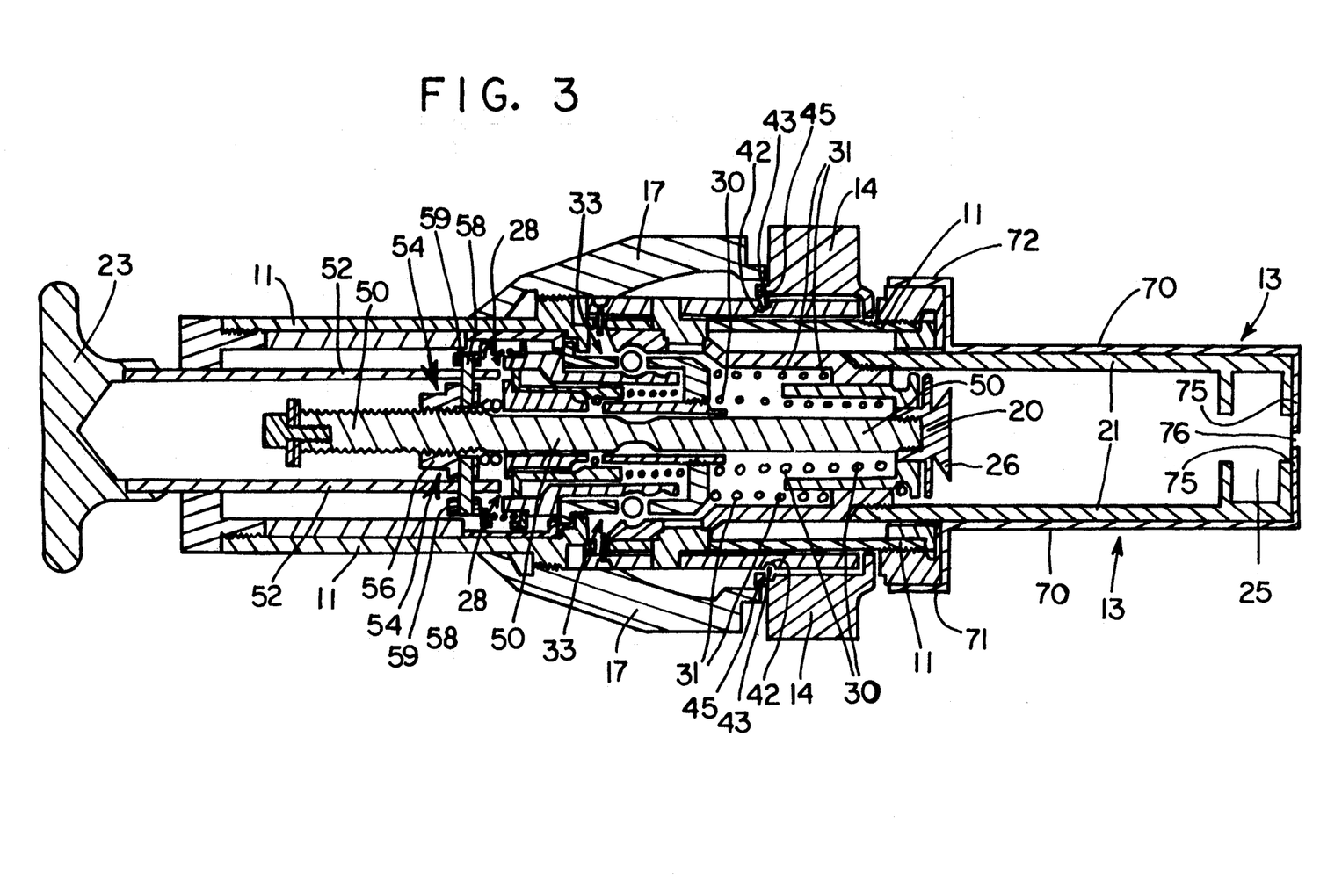
FIG. 3 is a cross sectional view of the biopsy device of the present invention taken along line 3—3 of FIG. 1.

Referring now to FIG. 3, there is shown a cross section through a tissue sampling apparatus that incorporates the improvements of the present invention. The tissue sampling apparatus or device shown in FIG. 3 comprises the following components that are disclosed and described fully in my previous U.S. Pat. No. 5,156,160. The device comprises an elongate housing 11 having a first end and a second end. A knob 23 is provided at the first or proximal end of the housing 15. A first piston 20 and a coaxial second piston 21 extend from the second end of the housing 11. A relatively small receiving well 25 having an open top is provided in the distal end of the second piston 21 for receiving a hub 15 on the proximal end of the outer, elongate cannula of the needle 12 to secure the hub 15 to the extending end of the second piston 21. A tenon 26 is located on an extending end of the first piston 20 for connecting to a mortise in the hub 16 on the proximal end of the elongate, inner rod of the needle 12 to the first piston 20. First and second springs 30 and 31 are located in the housing 11. The springs 30 and 31 bias the pistons 20 and 21 toward their distal position extending from the second end of the housing 11. Triggering means, shown generally by the arrow 28 in FIG. 3, is actuated by the distal end of the shaft 32 that extends from the knob 23 at the proximal end of the housing 11 to the interior of the housing 11. The triggering means 28 activates a motion imparting components, shown generally by the arrow 33 in FIG. 3, and motion imparting components release the pistons 20 and 21 to move in their successive movements so that the first piston 20 moves first to its fully extended position under the biasing force of the first spring 30 while the second piston 21 remains in its cocked position, and after the first piston 20 has moved to its fully extended position, the second piston 21 moves to its fully extended position under the biasing force of the second spring 31. All the components of the tissue sampling device or apparatus mentioned in this paragraph are shown and fully described in my previous U.S. Pat. No. 1,156,160, and that patent includes a complete explanation of all aspects of the tissue sampling device. The entire disclosure in U.S. Pat. No. 1,151,160 is included herein by reference, and for purposes of brevity, further description of the components of the tissue sampling device that are mentioned in this paragraph will not be given.

In accordance with the present invention an improvement in the means for cocking both the first and second pistons 20 and 21 is provided. In this improvement an annular, cocking ring 14 is positioned coaxially around the housing 11 near the second end of the housing 11. The annular, cocking ring 14 is adapted to be rotated about a longitudinal, central axis through the housing 11. Means are associated with the annular, cocking ring 14 for moving the second piston 21 into the housing 11 to its cocked position when the annular, cocking ring 14 is rotated. Means are further provided which are associated with the knob 23 on the first end of the housing 11 for moving the first piston 20 into the housing 11 to its cocked position when the knob 23 is pulled in a direction away from the first end of the housing 11.

Figure 4:
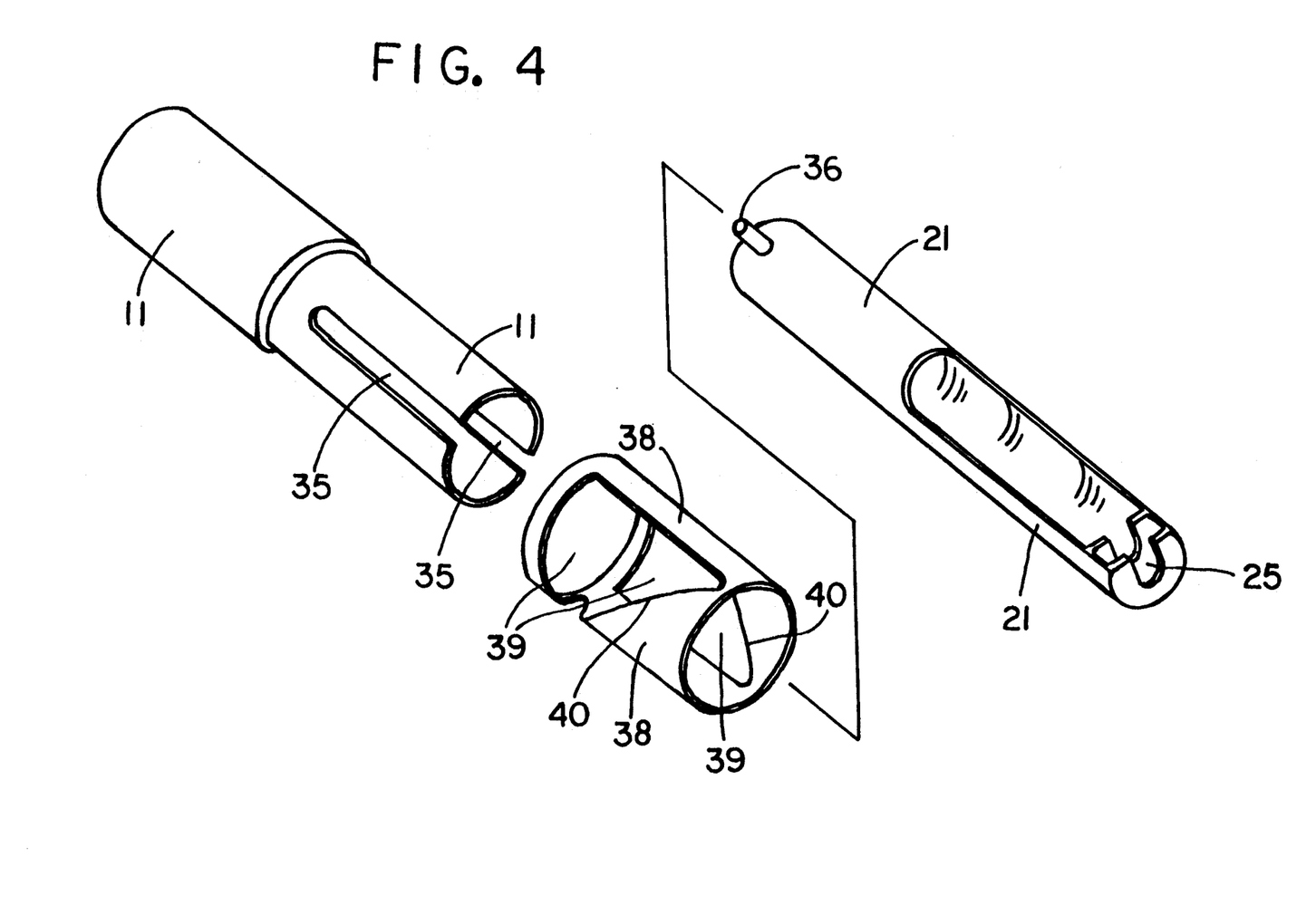
FIG. 4 is an exploded pictorial view of the housing, second piston and cylindrical cam member which is used in cocking the second piston.

As best shown in FIGS. 3 and 4, the means associated with the annular, cocking ring 14 for moving the second piston 21 into the housing 11 to its cocked position comprises at least one elongate slot 35 in the side of the housing 11, with the slot 35 having a first end positioned adjacent to the second end of the housing 11 and a second end spaced from the first end in direction toward the midsection of the housing 11. As illustrated there are preferably two elongate slots 35 and they are positioned diametrically on opposite sides of the housing 11.

A pin 36 is provided for each slot 35, with each pin 36 extending from the second piston 21 through a respective elongate slot 35. Each pin 36 is firmly attached to the second piston 21, and the pins 36 move back and forth in the elongate slot 35 as the second piston moves 21 into and out of the second end of the housing 11.

A rotating cylindrical member 38 is positioned coaxially about the housing 11 and between the housing 11 and the annular, cocking ring 14. A slanted cutout 39 is formed in the side of the rotating cylindrical member 38. The cutout 39 has one side that forms a curvilinear cam 40 in the surface of the rotating cylindrical member 38. The cam 40 extends partially around the rotating cylindrical member 38 and slants uniformly in a direction from one end of the rotating cylindrical member 38 to the other end of the rotating cylindrical member 38.

As illustrated, there are two cutouts 39 formed on opposite sides of the rotating cylindrical member 38, so that there is one cutout 39 and associated cam 40 for each of the pins 36 that extend from the second piston 21. Each of the pins 36 extend through the respective elongate slots 35 of the housing 11 and project into a respective cutout 39 in the rotating cylindrical member 38. When the rotating cylindrical member 38 is rotated each pin 36 is forced to move along the cam surface 40 as the rotating cylindrical member 38 rotates, whereby the pins 36 move upwardly in the slots 35 in a direction from the first ends of the slots 35 to the second ends of the slots 35 as the rotating cylindrical member 38 rotates.

Means are provided for moving the rotating cylindrical member 38 in its rotational movement as the annular, cocking ring 14 is rotated. Advantageously, the means for moving the rotating cylindrical member 38 as the annular, cocking ring 14 is rotated comprises a notch 42 on an outside surface of the rotating cylindrical member 38, and a projection 43 extending from the annular, cocking ring 14 that moves with the annular, cocking ring 14 and is received in the notch 42 on the outside surface of the rotating cylindrical member 38 to rotate the notating cylindrical member 38 when the annular, cocking ring 14 rotates.

In the embodiment of the invention illustrated in the drawings, a complementary notch 45 is formed on an inside surface of the annular, cocking ring 14, and the projection 43 extending from the annular, cocking ring 14 is a tab that fits in the complementary notch 45 of the annular, cocking ring 14. The tab forming the projection 43 is also received in the notch 42 on the outside surface of the rotating cylindrical member 38.

In the illustrated embodiment, the means associated with the knob 23 on the first end of the housing 11 for moving the first piston 20 into the housing 11 to its cocked position when the knob 23 is pulled comprises a center shaft 50 extending from the first piston 20 along the longitudinal centerline of the housing 11 toward the first end of the housing 11. Means are provided for engaging the center shaft 50 with the knob 23 whereby when the knob 23 is pulled in a direction away from the first end of the housing 11, the center shaft 50 moves longitudinally toward the first end of the housing 11 and pulls the first piston 20 inwardly into the housing 11 to its cocked position.

As illustrated in FIGS. 3 and 5, the means for engaging the center shaft 50 with the knob 23 comprises a hollow shaft 52 extending from the knob 23 into the housing 11 through the first end of the housing 11. The hollow shaft 52 fits coaxially over the center shaft 50 that extends from the first piston 20, and external threads are provided on the center shaft 52. A travel member 54 is provided having an internally threaded central opening such that the travel member 54 is threaded on the external threads of the center shaft 50. The travel member 54 can be threaded back and forth along the center shaft 50 by rotating the travel member 54 in one direction to advance toward the first piston 20 or in the opposite direction to withdraw or retract away from the first piston 20.

Means are provided for engaging the hollow shaft 52 that extends from the knob 23 with the travel member 54 such that when the hollow shaft 52 is rotated by the knob 23, the travel member 54 is also rotated. In addition, the travel member 54 is free to move back and forth longitudinally along the hollow shaft 52 as it is threaded back and forth on the external threads of the center shaft 50. Means are also provided for abutting an internal end of the hollow shaft 52 with the travel member 54 when the knob 23 is pulled in a direction away from the first end of the housing 11. The abutting internal end of the hollow shaft 52 engages the travel member 54 and pulls the travel member 54 and the center shaft 50 toward the first end of the housing 11. In turn, the center shaft 50 pulls the first piston 20 to its cocked position in the housing 11.

As best illustrated in FIGS. 3, 4 and 5, the center shaft 50 that extends from the first piston 20 at the other end of the housing 11 has external threads at its distal end near the first end of the housing 11. The external threads extend from the distal end of the center shaft 50 that is positioned near the first end of the housing 11, with the external threads extending along the center shaft 50 well into the housing 11 and at least slightly beyond the distal end of the hollow shaft 52 that extends into the housing 11. The hollow shaft 52 is provided with three elongate slots 60 that are parallel with each other and spaced equally from each other around the circumference of the hollow shaft 52.

As best shown in FIG. 5, the travel member 54 comprises a central hub 56 having a threaded central bore 57, whereby the threaded bore 57 is threaded on the threads of the center shaft 50. Three dowel-like projections 58 extend from the central hub 56 radially outwardly. These projections 58 are equally spaced form each other and extend through the respective slots 60 in the hollow shaft 52. An outer ring 59 is provided that fits over the perimeter of the hollow shaft 52. The projections 58 from the central hub 56 engage the outer ring 14 so as to be attached thereto. This in effect attaches the outer ring 59 integrally to the central hub 56.

As can be seen, the hollow shaft 52 can slide back and forth through the travel member 54, with the projections 58 of the travel member 54 sliding back and forth in the slots 60 of the hollow shaft 52. As the knob 23 and hollow shaft 52 are pulled from the first end of the housing 11, the distal ends of the slots 60 in the hollow shaft 52 engage the projections 58 on the travel member 54 and thus pull the travel member 54, the center shaft 50 and ultimately the first piston 20 toward the first end of the housing 11. This action accomplishes the cocking of the first piston 20.

As also can be seen from the drawings, rotation of the knob 23 and the hollow shaft 52 about a longitudinal axis through the hollow shaft 52 will also thread the travel member 52 back and forth along the threads of the center shaft 50. Thus, the amount of actual travel of the first piston 20 during its firing motion, i.e., the motion of the first piston 20 following triggering of the cocked device 10, can be controlled by setting the traveling member 52 at a desired position within its range of travel along the center shaft 50. The traveling member 52 is readily set in any desired position by rotating the knob 23 and threading the traveling member 52 along the center shaft 50.

To aid in determining the position of the traveling member 52 in its range of travel along the center shaft 50, it is advantageous to provide a transparent window 64 in the sidewall of the housing 11 so that one can see the position of the travel member 52 when the first piston 20 has been moved to its cocked position. It is advantageous to provide an indicia line 66 on the travel member 52 that is visible through the transparent window 64. It is also desirable to provide a set of scaled markings 68 on the transparent window 64 itself which form a gage to indicate the travel of the first piston 20 when the indicia line 66 registers with the scaled markings 68.

As mentioned previously, it is desirable to provide a removable cover 13 as shown in FIGS. 2 and 7 to cover the portions of the first and second pistons 20 and 21 as the device is being used to take a tissue sample. The cover 13 is made of a pliable plastic material and comprises a cylindrical member 70 that has a sufficient inside diameter and length to fit over the second piston 21 when the second piston 21 is extended to its furthest position from the end of the housing 11.

The cylindrical member 70 is cut down one longitudinal side thereof and a live hinge is formed in the diametrically opposite side of the cylindrical member 70. At the one end of the cylindrical member 70 that is to be positioned at the distal end of the housing 11 of the device 10, an enlarged annular channel 71 is provided that extends around one half of the one end of the cylindrical member 70. The channel 71 is integrally attached to the one end of the cylindrical member 70. A complementary annular channel 72 is attached by a live hinge to one of the ends of the annular channel 71. The annular channel 72 is adapted to be fit around a rim on the distal end of the housing 11 to surround one-half the perimeter of the rim, and the complementary annular channel 72 is then hinged down around the other portion of the perimeter of the rim on the distal end of the housing 11 to hold the cover 13 on the distal end of the housing 11. A snap catch can be incorporated in the free end of the complementary channel 72 that engages with the free end of the annular channel 71.

The distal ends of the two portions of the cylindrical member 70 are provided with semi-circular end caps 75, such that when the cylindrical member 70 is closed, the semi-circular end caps 75 form an end closure of the cylindrical member 70. Complementary notches 76 are formed in the respective, flat side edges of the semi-circular end caps 75 such that when the cylindrical member 70 is closed, the aligned notches 76 form an opening through which the needle 12 can extend as shown in FIG. 2. A snap catch 78 can be incorporated on the cut sides of the cylindrical member 70 to retain the cylindrical member 70 in a closed position after the hubs 15 and 16 of a needle 12 have been positioned in the hollow end of the second piston 21. The snap catch 78 can then be disengaged to open the cylindrical member 70 so as to allow removal of the needle 12 and replacement of it with another needle.

I claim:

1. In a tissue sampling apparatus of the type comprising (a) an elongate housing having a first end and a second end, (b) a knob at said first end of said housing, (c) a first piston and a coaxial second piston extending from the second end of said housing, (d) means on an extending end of said second piston for connecting a proximal end of an outer, elongate cannula to said extending end of said second piston, wherein the outer elongate cannula has a sharpened distal end for insertion into a sample target area of said tissue, (e) means on an extending end of said first piston for connecting a proximal end of an elongate, inner rod to said extending end of said first piston so that the inner rod, which has a sample receiving notch adjacent to its distal end, is received within said cannula, (f) first and second spring means in said housing, (g) cocking means for moving said first and second pistons in a longitudinal motion into said housing against the biasing force of said first and second spring, respectively, to cocked positions, and (h) triggering means for releasing said first and second pistons to move in successive movements out of said housing wherein the first piston moves first to its fully extended position under the biasing force of said first spring while said second piston remains in its cocked position, and after the first piston has moved to its fully extended position, the second piston moves to its fully extended position under the biasing force of said second spring, an improvement in the cocking means wherein said first and second pistons are moved to their cocked positions in separate distinct operations, said improvement comprising an annular ring positioned coaxially around said housing near the second end of said housing, with said annular ring being able to rotate about a longitudinal axis through said housing;

means associated with said annular ring for moving said second piston into said housing to its cocked position when said annular ring is rotated; and means associated with said knob on said first end of said housing for moving said first piston into said housing to its cocked position when said knob is pulled in a direction away from said first end of said housing.

2. An improvement in a tissue sampling apparatus in accordance with claim 1, wherein said means associated with said annular ring for moving said second piston into said housing to its cocked position comprises an elongate slot in the side of said housing, said slot having a first end positioned adjacent to said second end of said housing and a second end spaced from said first end in direction toward the midsection of said housing;

an pin extending from said second piston through said elongate slot, wherein said pin moves back and forth in said elongate slot as said second piston moves into and out of said second end of said housing;

a rotating cylindrical member positioned coaxially about said housing and between said housing and said annular ring;

a slanted cutout in the side of said rotating cylindrical member that forms a curvilinear cam in the surface of said rotating cylindrical member, with said cam extending partially around said rotating cylindrical member and slanting uniformly in a direction from one end of said rotating cylindrical member to the other end of said rotating cylindrical member, wherein said pin extending through said elongate slot of said housing is forced to move along the cam surface as said rotating cylindrical member rotates so that said pin moves upwardly in said slot in a direction from said first end of said slot to said second end of said slot as said rotating cylindrical member rotates; and means are provided for moving the rotating cylindrical member in its rotational movement as said annular ring is rotated.

3. An improvement in a tissue sampling apparatus in accordance with claim 2 wherein the means for moving the rotating cylindrical member as said annular ring is rotated comprises a notch on an outside surface of said rotating cylindrical member; and a projection extending from said annular ring that moves with said annular ring and is received in said notch on the outside surface of said rotating cylindrical member to rotate the notating cylindrical member when the annular ring rotates.

4. An improvement in a tissue sampling apparatus in accordance with claim 3 wherein a complementary notch is formed on an inside surface of said annular ring and said projection extending from said annular ring is a tab that fits in the complementary notch of said annular ring and is also received in the notch on the outside surface of said rotating cylindrical member.

5. An improvement in a tissue sampling apparatus in accordance with claim 1 wherein said means associated with said knob on said first end of said housing for moving said first piston into said housing to its cocked position when said knob is pulled comprises a center shaft extending from said first piston along the longitudinal centerline of said housing toward said first end of said housing; and means for engaging said center shaft with said knob whereby when said knob is pulled in a direction away from said first end of said housing, the center shaft moves longitudinally toward said first end of said housing and pulls said first piston inwardly into said housing to its cocked position.

6. An improvement in a tissue sampling apparatus in accordance with claim 5 wherein said means for engaging said center shaft with said knob comprises a hollow shaft extending from said knob into said housing through said first end of said housing, with said hollow shaft fitting coaxially over said center shaft that extends from said first piston;

external threads on said center shaft that extends from said first piston;

a travel member having an internally threaded central opening such that said travel member is threaded on the external threads of said center shaft and can be moved back and forth along said center shaft by rotating said travel member to advance toward said first piston or retract away from said first piston;

means for engaging said hollow shaft that extends from said knob with said travel member whereby said hollow shaft will rotate said travel member when said hollow shaft is rotated by said knob but said travel member is free to move back and forth longitudinally along said hollow shaft as it moves back and forth on the external threads of said center shaft; and means for abutting an internal end of said hollow shaft with said travel member when said knob is pulled in a direction away from said first end of said housing so that said travel member and said center shaft move toward said first end of said housing and pulls said first piston inwardly into said housing to its cocked position, whereby the travel of said first piston during its movement out of said housing after activating said triggering means can be adjusted by rotating said knob to move said travel member to a desired position on said center shaft just prior to activating said triggering means.

7. An improvement in a tissue sampling apparatus in accordance with claims 6 wherein a transparent window is provided in the sidewall of said housing so that one can see the position of said travel member on said center shaft when said first piston has been moved to its cocked position.

8. An improvement in a tissue sampling apparatus in accordance with claim 7 wherein an indicia line on said travel member is visible through said transparent window and a set of scaled markings are provided on said window which correspond to the travel of said first piston when said indicia line registers with said scaled markings.

* * * * *